United States Patent [19]

Soloway

[11] Patent Number: 4,574,784
[45] Date of Patent: Mar. 11, 1986

[54] LARYNGOSCOPE

[76] Inventor: David J. Soloway, 22 Alice Ave., Merrick, N.Y. 11566

[21] Appl. No.: 647,188

[22] Filed: Sep. 4, 1984

[51] Int. Cl.⁴ .............................................. A61B 1/06
[52] U.S. Cl. ..................................................... 128/11
[58] Field of Search ...................... 128/11, 10, 15, 16, 128/17, 18, 4, 6

[56] References Cited

U.S. PATENT DOCUMENTS

| | | | |
|---|---|---|---|
| 2,433,705 | 12/1947 | Palmeter | 128/10 |
| 2,646,037 | 7/1953 | Cook et al. | 128/6 |
| 2,649,087 | 8/1953 | Allyn et al. | 128/6 |
| 4,273,112 | 6/1981 | Heine et al. | 128/11 |
| 4,406,280 | 9/1983 | Upsher | 128/11 |
| 4,437,458 | 3/1984 | Upsher | 128/11 |

Primary Examiner—William H. Grieb
Attorney, Agent, or Firm—Michael I. Kroll

[57] ABSTRACT

An improved laryngoscope is provided and consists of an angle adjustable adapter connected between a handle and a blade or the handle itself being angle adjustable so that various angle arrangements can be formed by the blade with respect to the handle. The improved laryngoscope heretofore described permits interchangability between conventional and fiber-optic lighting systems of which the components thereof assemble to form a complete mixed system.

18 Claims, 20 Drawing Figures

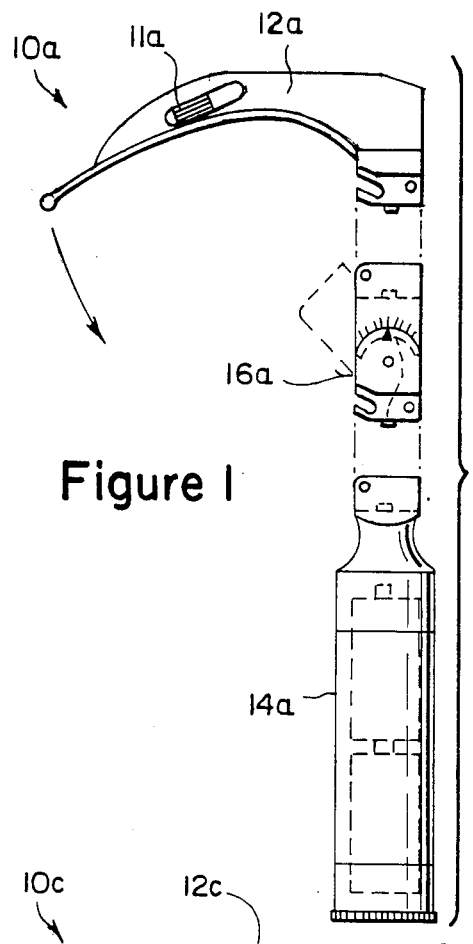
Figure 1
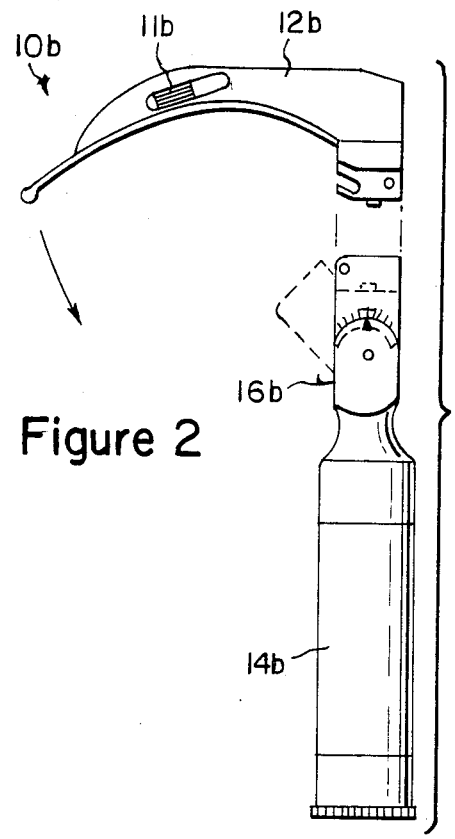
Figure 2
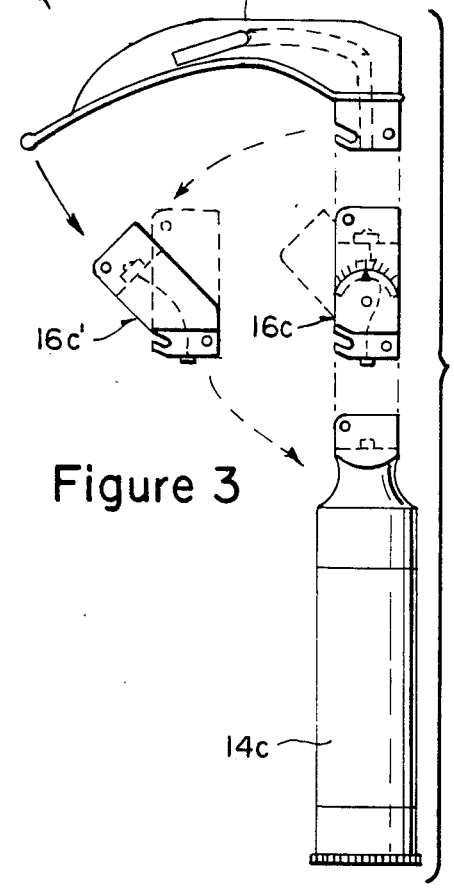
Figure 3
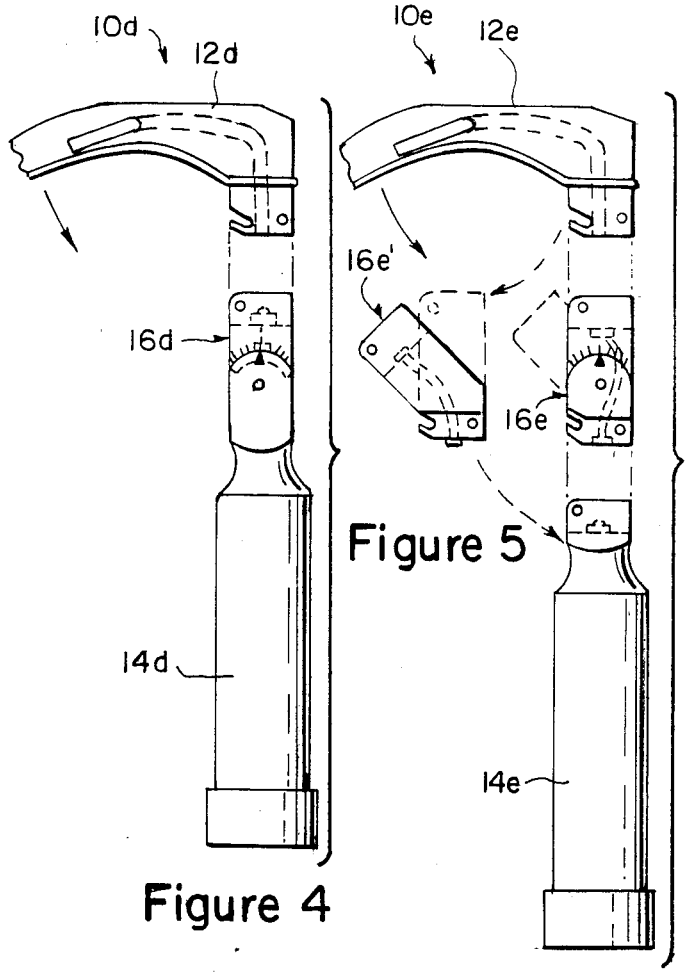
Figure 4
Figure 5

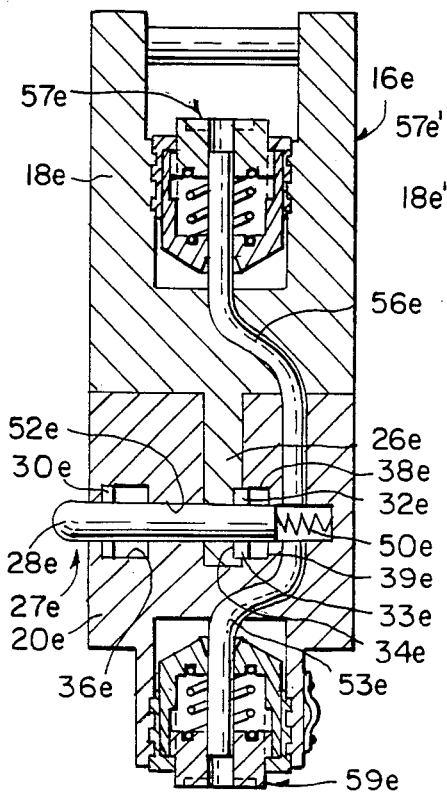
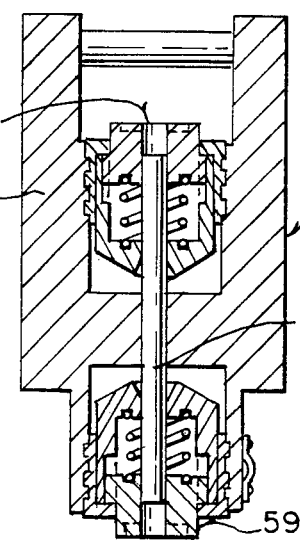
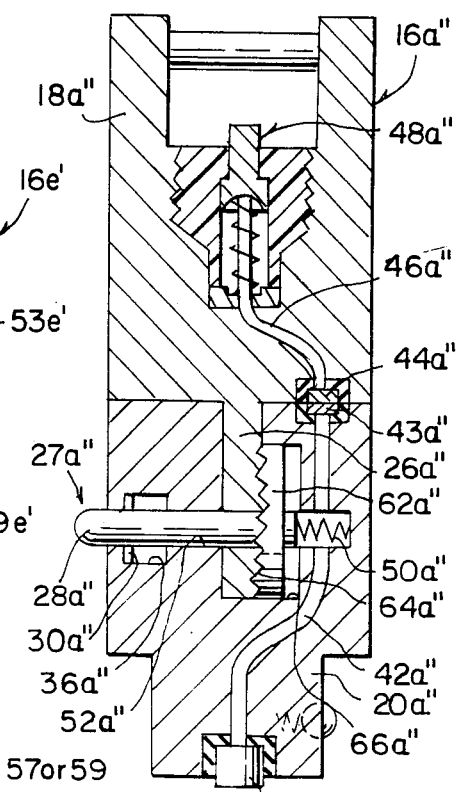
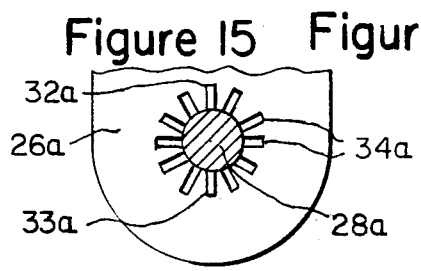
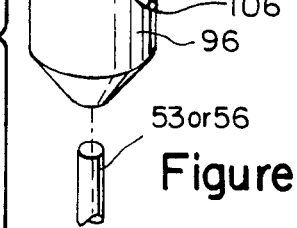
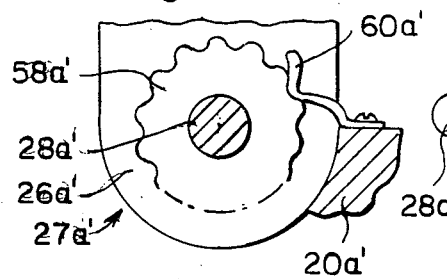
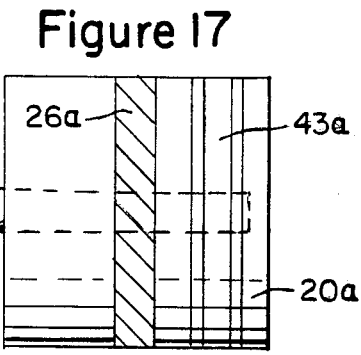

LARYNGOSCOPE

BACKGROUND OF THE INVENTION

1. Field of Invention

The instant invention relates generally to laryngoscopes and more specifically it relates to an improved laryngoscope.

The laryngoscope is used to visualize the larynx and its surrounding structures. Most commonly this is done for the purpose of inserting a tube through the glottis, a procedure called endotracheal intubation. Most laryngoscopes in use today consists of two basic parts: the handle and blade and come in a conventional illumination system or a fiber-optic illumination system.

The handle is used to hold the laryngoscope and has a rough surface for traction and houses the batteries for the light source. The connection point between the handle and the blade is called the fitting with a hook-on fitting most commonly used. The fitting is positioned at the end of the handle at a fixed 90° angle to the long axis of the handle to facilitate exchange of blades. The blade is the part of the laryngoscope which is inserted into the mouth and has a light source for visualizing the larynx and its surrounding structures.

In the conventional illumination system a bulb is placed in the distal third of the blade and electric contact is made through the fitting with a circuit formed when the blade is in position for use.

In the fiber-optic illumination system all electrical contacts, bulb and batteries are located in the handle. Illumination is provided by a fiber-optic light guide in the blade, receiving light from the bulb in the handle and transmitting it to provide cold illumination of the larynx during use.

2. Description of the Prior Art

Numerous laryngoscope blades have been provided in prior art that are adapted to visualize the larynx and its surrounding structures. There are certain situations, where laryngoscopy is difficult and where one type of laryngoscope blade may be particularly advantageous. This has led to the development of a large number of laryngoscope blades, each with its own claimed advantages. While these units may be suitable for the particular purpose to which they address, they would not be suitable for the purposes of the present invention as heretofore described.

SUMMARY OF THE INVENTION

A principle object of the present invention is to provide an improved laryngoscope that uses an adapter with an angle adjustable fitting; this adapter is connected between a handle and a blade so that various angle arrangements can be formed by the blade with respect to the handle, thereby facilitating endotracheal intubation precarious situations.

Another object is to provide an improved laryngoscope that uses an adjustable handle connected to a blade so that various angle arrangements can be formed by the blade with respect to the handle.

An additional object is to provide an improved laryngoscope that uses an adapter for connecting a conventional laryngoscope handle to a fiber-optic blade so they can be used as a complete system.

A further object is to provide an improved laryngoscope that uses an adaper for connecting a conventional laryngoscope handle to a plastic disposable fiber-optic blade so that sanitary practice is more rigidly adhered to.

A still further object is to provide an improved laryngoscope that is easy to use, is economical in cost and conforms to safety performance and durability throughout its entire operation.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is an exploded side view of a conventional illumination system having an adjustable adapter.

FIG. 2 is an exploded side view of a conventional illumination system having an adjustable handle.

FIG. 3 is an exploded side view of a handle from a conventional illumination system and a fiber-optic blade having an angle adjustable adapter or a fixed angle adapter.

FIG. 4 is an exploded side view of a fiber-optic illumination system having an adjustable handle.

FIG. 5 is an exploded side view of a fiber-optic illumination system having an angle adjustable adapter or a fixed angle adapter.

FIG. 12 is a cross-sectional view of the angle adjustable adapter shown in FIG. 5.

FIG. 13 is a cross-sectional view of the fixed angle adapter shown in FIG. 5.

FIG. 14 is a cross-sectional view similar to FIG. 7 showing a modification of the adjustment device.

FIG. 15 is a partial cross-sectional view taken along line 15—15 in FIG. 7.

FIG. 15A is a partial cross-sectional view similar to FIG. 15 showing another modification of the adjustment device.

FIG. 16 is a perspective view of the shaft shown in FIG. 7.

FIG. 17 is a cross-sectional view taken along line 17—17 in FIG. 7.

FIG. 18 is an exploded perspective view of the light bulb and switch assembly shown in FIGS. 9, 10 and 11.

FIG. 19 is an exploded perspective view of the light gasket and spring assembly shown in FIGS. 12 and 13.

DESCRIPTION OF THE PREFERRED EMBODIMENTS

Figure 6:
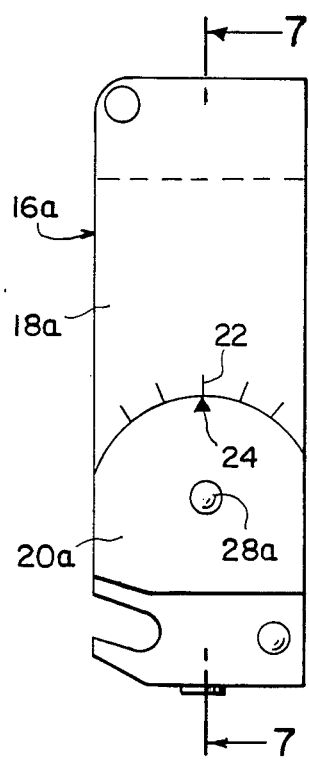
FIG. 6 is an enlarged side view of the adjustable adapter shown in FIG. 1.

Turning now descriptively to the drawings, in which similar reference characters denote similar elements throughout the several views, FIGS. 1, 3 and 5 illustrate an improved laryngoscope 10a, 10c and 10e, each having a hook-on fitting handle 14a, 14c and 14e and a hook-on fitting blade 12a, 12c and 12e respectively. FIGS. 1, 3 and 5 demonstrate that the invention consists of a hook-on fitting angle adjustable adapter 16a, 16c and 16e connected between the handle 14a, 14c and 14e and the blade 12a, 12c and 12e respectively so that various angle arrangements can be formed by the blade with respect to the handle.

FIGS. 2 and 4 illustrates an improved laryngoscope 10b and 10d respectively, each having a hook-on fitting handle 14b and 14d and a hook-on fitting blade 12b and 12d respectively. FIGS. 2 and 4 demonstrate that the invention consists of the handle 14b and 14d being angle adjustable at 16b and 16d respectively so that various angle arrangements can be formed by the blade with respect to the handle.

FIGS. 1 and 2 illustrate laryngoscopes 10a and 10b respectively with conventional illumination systems. FIGS. 4 and 5 illustrate laryngoscopes 10d and 10e respectively with fiber-optic illumination systems. FIG. 3 illustrates that laryngoscope 10c is a complete mixed system produced by insertion of the adapters shown and consists of a handle 14c from a conventional illumination system and a blade 12c from a fiber-optic illumination system. The angle adjustable adapter 16c in FIG. 3 can be substituted by a fixed angle adapter 16c' connected between the conventional handle 14c and the fiber-optic blade 12c, so that the handle and the blade can be used together as a complete system. The angle adjustable adapter 16e in FIG. 5 can be substituted by a fixed angle adapter 16e' connected between the fiber-optic handle 14e and the fiber-optic blade 12e.

Figure 7:
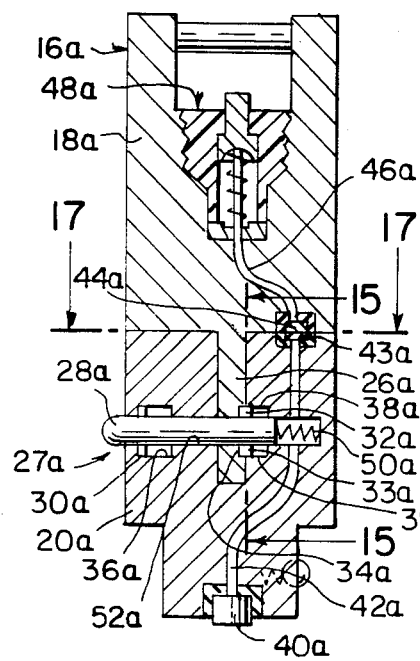
FIG. 7 is a cross-sectional view taken along line 7—7 in FIG. 6.

FIGS. 6, 7, 15, 16 and 17 illustrates the adapter 16a in greater detail. As best seen in FIG. 6 the adapter 16a consists of an upper half 18a and a lower half 20a. The upper half 18a has angle indications 22 marked on its outer wall thereof while the lower half 20a has a fixed pointer 24 on its outer wall thereof. As best seen in FIG. 7 an arm 26a from upper half 18a extends into the lower half 20a and is captured within by an adjustment device 27a, so that the upper half 18a can pivot around the lower half 20a. The adjustment device 27a as shown in FIG. 7 is identical with the adjustment devices 27b through 27d as shown in FIGS. 8, 9, 11 and 12 respectively, therefore it will be described as follows:

The adjustment device 27a consists of a shaft 28a having a transverse pin 30a at one end and a pair of opposite placed teeth 32a and 33a at other end in alignment with the pin 30a. The shaft 28a slides within an aperture 52a in the lower half 20a and is spring loaded with spring 50a so that the shaft 28a extends out of one side of the lower half 20a. The pin 30a slides in slot 36a, tooth 32a slides in slot 38a and tooth 33a slides in slot 39a. The arm 26a has a plurality of radiating teeth recesses 34a around the shaft 28a (see FIG. 15). When the shaft 28a is manually pressed in, the teeth 32a and 33a will move away from each recess 34a that they were in. When the upper half 18a is turned the shaft 28a is manually released and the spring 50a will push the shaft 28a back so that the teeth 32a and 33a will enter different recesses 34a to lock in.

In FIG. 15A the adjustment device 27a' can substitute the adjustment device 27a shown in FIG. 7 and consists of a wheel 58a' having a plurality of indentations around its periphery. The wheel 58a' is affixed to arm 26a'. A spring pawl 60a' is affixed to the lower half 20a' and engages one of the indentations on the wheel 58a' so that when the upper half is turned the spring pawl 60a' will enter another indentation on the wheel to lock in the upper half to a new angle.

In the adapter 16a, shown in FIG. 7, the lower half 20a has a lower contact pin 40a, wire 42a and an upper curved slide contact 43a. The upper half 18a has a lower contact pin 44a, a wire 46a and an upper contact pin 48a. When the upper half 18a is turned about the lower half 20a electrical contact between the handle 14a and the blade 12a is maintained.

Figure 9:
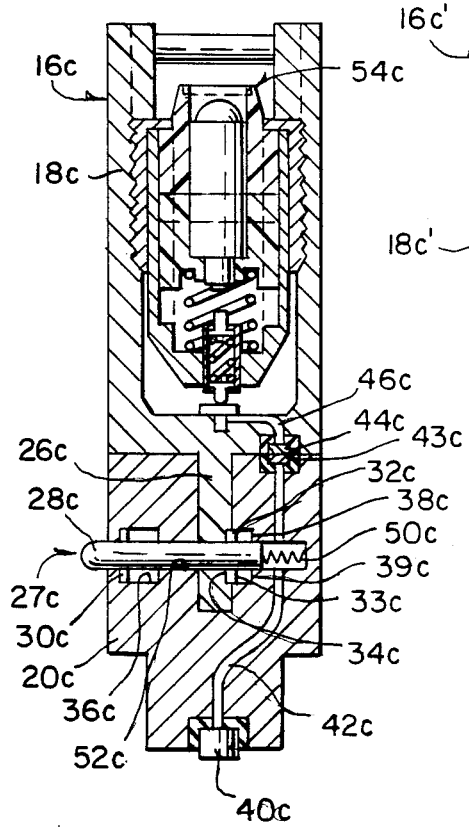
FIG. 9 is a cross-sectional view of the angle adjustable adapter shown in FIG. 3.

In adapter 16c, shown in FIG. 9, the upper half 18c substitutes a light bulb with switch 54c, for the upper contact pin.

In adapter 16e, shown in FIG. 12, a lower light gasket with spring 59e in the lower half 20e is connected to a flexible fiber-optic tube 56e having a flexible opaque insulator 53e. The fiber-optic tube extends into the upper half 18e and is connected to an upper light gasket with spring 57e.

Figure 10:
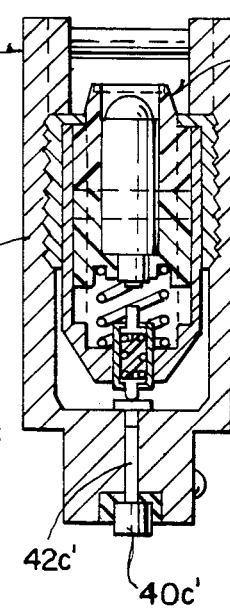
FIG. 10 is a cross-sectional view of the fixed angle adapter shown in FIG. 3.

In adapter 16c', shown in FIG. 10, the lower contact pin 40c' is connected by wire 42c' directly to a light bulb with switch 54c'.

In adapter 16e', shown in FIG. 13, the lower light gasket with spring 59e' connected by flexible opaque insulator 53e' directly to an upper light gasket with spring 57e'.

The adapter 16a", shown in FIG. 14, is identical to adapter 16a in FIG. 7 but has a different adjustment device 27a". A thread wheel 62a" is affixed to the shaft 28a" within slot 66a". Teeth 64a" are placed on one side of arm 26a" so that when the shaft 28a" is now manually pressed the thread wheel 62a" will disengage from the teeth 64a" so that arm 26a" can turn.

Figure 8:
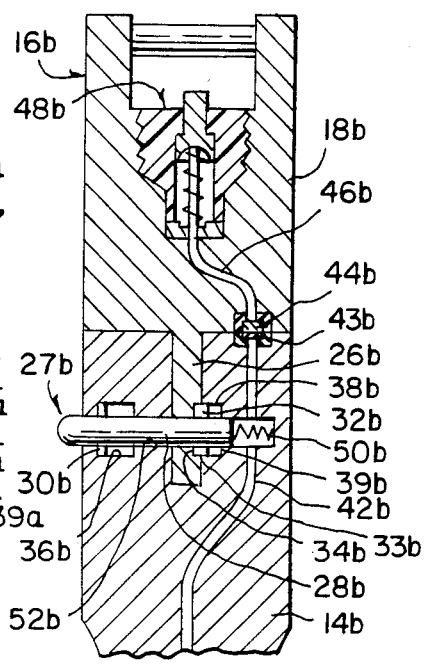
FIG. 8 is a partial cross-sectional view of the adjustable handle shown in FIG. 2.

In FIG. 8 the adjustable upper portion 16b of handle 14b is similar to adapter 16a, shown in FIG. 7, but does not have the lower contact pin. Instead the wire 42b is directly connected to the batteries.

Figure 11:
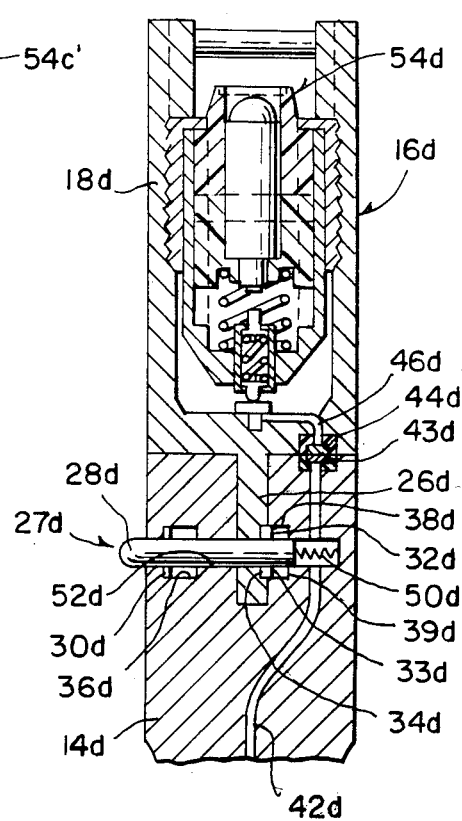
FIG. 11 is a partial cross-sectional view of the adjustable handle shown in FIG. 4.

In FIG. 11 the adjustable upper portion 16d of handle 14d is similar to adapter 16c, shown in FIG. 3, but does not have the lower contact pin. Instead the wire 42d is directly connected to the batteries.

FIG. 18 shows a light bulb and switch assembly 54 that is typical for FIGS. 9, 10 and 11. The assembly 54 consists of a threaded cap 70, upper bulb housing 72, light bulb 73, lower bulb housing 74, spring 76 and case 78. The cap 70 has a large central hole 36 so that the upper bulb housing 72 can fit into it. The bulb 73 fits within hole 84 having a top slot in upper bulb housing 72 and within hole 82 in lower bulb housing 74 and is anchored into the lower bulb housing. The notch 75 on upper bulb housing 72 engages notch 77 on lower bulb housing 74. As also may be seen from FIG. 18 the spring 76 enters aperture 80 in case 78 to bias the upper bulb housing 72 and lower bulb housing 74. The cap 70 engages the case 78 whereby transverse pin 79 is in engagement with L-shaped slot 71 on cap 70 to complete the assembly. The assembly 54 can then be threaded into upper half 18.

FIG. 19 shows a light gasket and spring assembly 57 or 59 that is typical for FIGS. 12 and 13. The assembly 57 or 59 consists of a threaded cap 90, fiber-optic housing 92, spring 94 and case 96. The cap 90 has a large central hole 98 so that the fiber-optic housing 92 can fit into it. The spring 94 enters aperture 104 in case 96 to bias the fiber-optic housing 92 when the notch 102 on the fiber-optic housing 92 engages the notched aperture 104 on case 96. The case 96 with transverse pin 106 is in engagement with L-shaped slot 91 on cap 90 to complete the assembly. The assembly 57 can then be threaded into upper half 18 and the assembly 59 can then be threaded into lower half 20 with the fiber-optic tube 53 or 56 entering hole 100 in the fiber-optic housing 92.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An improved laryngoscope of the type having a hook-on fitting handle and a hook-on fitting blade wherein the improvement comprises a hook-on fitting angle adjustable adapter connected between said handle and said blade so that various angle arrangements can be formed by said blade with respect to said handle, said hook-on fitting angle adjustable adapter comprising a lower half having a slot therein, an upper half having an arm extending into said slot of said lower half, and an adjustable device to capture said arm so that said upper half can pivot around said lower half.

2. An improved laryngoscope as recited in claim 1, wherein said laryngoscope is of a conventional illumination system.

3. An improved laryngoscope as recited in claim 1, wherein said laryngoscope is of a fiber-optic illumination system.

4. An improved laryngoscope as recited in claim 1, wherein said laryngoscope is of a mixed illumination system with said handle being of a conventional illumination system and said blade being of a fiber-optic illumination system.

5. An improved laryngoscope as recited in claim 1, wherein said adjustment device comprises a shaft having a transverse pin at one end and a pair of opposite placed teeth at other end in alignment with said pin, said shaft slides within an aperture in said lower half and is spring loaded with a spring so that said shaft extends out of one side of said lower half, said pin slides in first slot, first tooth slides in second slot and second tooth slides in third slot, said arm having a plurality of radiating teeth recesses around said shaft, when said shaft is manually pressed in, said teeth will move away from each said recess that they were in, when said upper half is turned said shaft is manually released and said spring will push said shaft back so that said teeth will enter different said recesses to lock in.

6. An improved laryngoscope as recited in claim 1, wherein said adjustment device comprises a shaft having a transverse pin at one end and a wheel having a plurality of radiating teeth at other end opposite said pin, said shaft slides within an aperture in said lower half and is spring loaded with a spring so that said shaft extends out of one side of said lower half, said pin slides in first slot and said wheel slides in second slot, said arm having a plurality of radiating teeth around said shaft to engage said teeth of said wheel, when said shaft is manually pressed in, said wheel will move away from said teeth in said arm that they were in, when said upper half is turned said shaft is manually released and said spring will push said shaft back so that said teeth of said wheel will engage different teeth on said arm to lock in.

7. An improved laryngoscope as recited in claim 1, wherein said adjustment device comprises:

(a) a wheel having a plurality of indentations around its periphery, said wheel is affixed to said arm; and
(b) a spring pawl affixed to said lower half and engage one of said indentations on said wheel so that when said upper half is turned said spring pawl will enter another indentation on said wheel to lock in said upper half to a new angle.

8. An improved laryngoscope as recited in claim 1, wherein said adapter further comprises:

(a) said lower half having a lower contact pin, an upper convexly curved slide contact and a wire connected therebetween; and
(b) said upper half having a lower concavely curved slide contact, an upper contact pin and a wire connected therebetween so that when said upper half is turned about said lower half electrical contact between said handle and said blade is mantained.

9. An improved laryngoscope as recited in claim 1, wherein said adapter further comprises:

(a) said lower half having a lower contact pin, an upper convexly curved slide contact and a wire connected therebetween; and
(b) said upper half having a lower concavely curved slide contact, an upper light bulb with switch, and a wire connected therebetween so that when said upper half is turned about said lower half electrical contact between said handle and said light bulb is maintained.

10. An improved laryngoscope as recited in claim 1, wherein said adapter further comprises:

(a) a lower light gasket with spring in said lower half;
(b) an upper light gasket with spring in said upper half; and
(c) a flexible fiber-optic tube having a flexible opaque insulator, said fiber-optic tube connected between said lower light gasket and said upper light gasket so that when said upper half is turned about said lower half fiber-optic light between said handle and said blade is maintained.

11. An improved laryngoscope of the type having a hook-on fitting handle and a hook-on fitting blade wherein the improvement comprises said handle being angle adjustable so that various angle arrangements can be formed by said blade with respect to said handle, said handle having an angle adjustable portion comprising a lower half having a slot therein, an upper half having an arm extending into said slot of said lower half, and an adjustment device to capture said arm so that said upper half can pivot around said lower half.

12. An improved laryngoscope as recited in claim 11, wherein said laryngoscope is of a conventional illumination system.

13. An improved laryngoscope as recited in claim 11, wherein said laryngoscope is of a fiber-optic illumination system.

14. An improved laryngoscope as recited in claim 11, wherein said adjustment device comprises a shaft having a transverse pin at one end and a pair of opposite placed teeth at other end in alignment with said pin, said shaft slides within an aperture in said lower half and is spring loaded with a spring so that said shaft extends out of one side of said lower half, said pin slides in first slot, first tooth slides in second slot and second tooth slides in third slot, said arm having a plurality of radiating teeth recesses around said shaft, when said shaft is manually pressed in, said teeth will move away from each said recess that they were in, when said upper half is turned said shaft is manually released and said spring will push said shaft back so that said teeth will enter different said recesses to lock in.

15. An improved laryngoscope as recited in claim 11, wherein said adjustment device comprises a shaft having a transverse pin at one end and a wheel having a plurality of radiating teeth at other end opposite said pin, said shaft slides within an aperture in said lower half and is spring loaded with a spring so that said shaft extends out of one side of said lower half, said pin slides in first slot and said wheel slides in second slot, said arm having a plurality of radiating teeth around said shaft to engage said teeth of said wheel, when said shaft is manually pressed in, said wheel will move away from said teeth in said arm that they were in, when said upper half is turned said shaft is manually released and said spring will push said shaft back so that said teeth of said wheel will engage different teeth on said arm to lock in.

16. An improved laryngoscope as recited in claim 11, wherein said adjustment device comprises:
   (a) a wheel having a plurality of indentations around its periphery, said wheel is affixed to said arm; and
   (b) a spring pawl affixed to said lower half and engage one of said indentations on said wheel so that when said upper half is turned said spring pawl will enter another indentation on said wheel to lock in said upper half to a new angle.

17. An improved laryngoscope as recited in claim 11, wherein said adjustable portion of said handle further comprises:
   (a) said lower half having a lower battery contact pin, an upper convexly curved slide contact and a wire connected therebetween; and
   (b) said upper half having a lower concavely curved slide contact, an upper contact pin and a wire connected therebetween so that when said upper half is turned about said lower half electrical contact between said handle and said blade is maintained.

18. An improved laryngoscope as recited in claim 1, wherein said adjustable portion of said handle further comprises:
   (a) said lower half having a lower battery contact pin, an upper convexly curved slide contact and a wire connected therebetween; and
   (b) said upper half having a lower concavely curved slide contact, an upper light gasket and light bulb with switch, and a wire connected therebetween so that when said upper half is turned about said lower half electrical contact between said handle and said light bulb is maintained.

* * * * *